US009839480B2

(12) United States Patent
Pribanic et al.

(10) Patent No.: US 9,839,480 B2
(45) Date of Patent: Dec. 12, 2017

(54) SURGICAL ADAPTER ASSEMBLIES FOR USE BETWEEN SURGICAL HANDLE ASSEMBLY AND SURGICAL END EFFECTORS

(71) Applicant: COVIDIEN LP, Mansfield, MA (US)

(72) Inventors: Russell Pribanic, Roxbury, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 1093 days.

(21) Appl. No.: 13/904,497

(22) Filed: May 29, 2013

(65) Prior Publication Data

US 2014/0012237 A1    Jan. 9, 2014

Related U.S. Application Data

(60) Provisional application No. 61/669,208, filed on Jul. 9, 2012.

(51) Int. Cl.
*A61B 17/00* (2006.01)
*A61B 17/56* (2006.01)
(Continued)

(52) U.S. Cl.
CPC ............ *A61B 19/22* (2013.01); *A61B 17/068* (2013.01); *A61B 17/07207* (2013.01);
(Continued)

(58) Field of Classification Search
CPC ... A61B 17/07207; A61B 17/32; A61B 17/34; A61B 17/68; A61B 17/1155; A61B 19/2203
(Continued)

(56) References Cited

U.S. PATENT DOCUMENTS 2,777,340 A    1/1957  Hettwer et al.
2,957,353 A    10/1960 Babacz
(Continued)

FOREIGN PATENT DOCUMENTS

AU    2008229795 A1    4/2009
CA       2451558 A1    1/2003
(Continued)

OTHER PUBLICATIONS

Australian Patent Examination Report No. 1, dated Nov. 27, 2016, corresponding to Australian Applicaiton No. 2013206350; 3 pages.
(Continued)

*Primary Examiner* — Anhtuan T Nguyen
*Assistant Examiner* — William Chou

(57) ABSTRACT

An adapter assembly is provided for selectively interconnecting a surgical end effector that is configured to perform a function and a surgical device that is configured to actuate the end effector, the end effector including at least one axially translatable drive member, and the surgical device including at least one rotatable drive shaft. The adapter assembly includes at least one drive converter assembly including a drive shaft; a drive coupling nut threadably connected to a distal end portion of the drive shaft; and an axially translatable drive bar connected to the drive coupling nut, wherein rotation of the drive shaft results in axial translation of the drive bar. The drive coupling nut engages 29 teeth of the threaded distal end portion of the drive shaft. The drive coupling nut is manufactured from unreinforced PEEK thermoplastic polymer.

11 Claims, 9 Drawing Sheets

(51) Int. Cl.
*A61B 17/58* (2006.01)
*A61F 2/30* (2006.01)
*A61B 19/00* (2006.01)
*A61B 17/285* (2006.01)
*A61B 17/068* (2006.01)
*A61B 17/072* (2006.01)
*A61B 17/29* (2006.01)

(52) U.S. Cl.
CPC .... *A61B 17/285* (2013.01); *A61B 2017/0046* (2013.01); *A61B 2017/00367* (2013.01); *A61B 2017/00398* (2013.01); *A61B 2017/00464* (2013.01); *A61B 2017/00473* (2013.01); *A61B 2017/00477* (2013.01); *A61B 2017/00526* (2013.01); *A61B 2017/00831* (2013.01); *A61B 2017/2903* (2013.01)

(58) Field of Classification Search
USPC ...... 600/1, 75, 130, 169, 185, 205, 206, 207, 600/219; 227/175.2, 181.1
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |

(56) References Cited

U.S. PATENT DOCUMENTS

| | | | |
|---|---|---|---|
| 7,341,295 B1 * | 3/2008 | Veatch | A61F 2/588 294/106 |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,407,078 B2 | 8/2008 | Shelton, IV et al. | |
| 7,416,101 B2 | 8/2008 | Shelton, IV et al. | |
| 7,419,080 B2 | 9/2008 | Smith et al. | |
| 7,422,139 B2 | 9/2008 | Shelton, IV et al. | |
| 7,431,189 B2 | 10/2008 | Shelton, IV et al. | |
| 7,441,684 B2 | 10/2008 | Shelton, IV et al. | |
| 7,448,525 B2 | 11/2008 | Shelton, IV et al. | |
| 7,464,846 B2 | 12/2008 | Shelton, IV et al. | |
| 7,464,847 B2 | 12/2008 | Viola et al. | |
| 7,464,849 B2 | 12/2008 | Shelton et al. | |
| 7,481,347 B2 | 1/2009 | Roy | |
| 7,481,824 B2 | 1/2009 | Boudreaux et al. | |
| 7,487,899 B2 | 2/2009 | Shelton, IV et al. | |
| 7,549,564 B2 | 6/2009 | Boudreaux | |
| 7,565,993 B2 | 7/2009 | Milliman et al. | |
| 7,568,603 B2 | 8/2009 | Shelton, IV et al. | |
| 7,575,144 B2 | 8/2009 | Ortiz et al. | |
| 7,588,175 B2 | 9/2009 | Timm et al. | |
| 7,588,176 B2 | 9/2009 | Timm et al. | |
| 7,637,409 B2 | 12/2009 | Marczyk | |
| 7,641,093 B2 | 1/2010 | Doll et al. | |
| 7,644,848 B2 | 1/2010 | Swayze et al. | |
| 7,670,334 B2 | 3/2010 | Hueil et al. | |
| 7,673,780 B2 | 3/2010 | Shelton, IV et al. | |
| 7,699,835 B2 | 4/2010 | Lee et al. | |
| 7,721,931 B2 | 5/2010 | Shelton, IV et al. | |
| 7,738,971 B2 | 6/2010 | Swayze et al. | |
| 7,740,159 B2 | 6/2010 | Shelton, IV et al. | |
| 7,743,960 B2 | 6/2010 | Whitman et al. | |
| 7,758,613 B2 | 7/2010 | Whitman | |
| 7,766,210 B2 | 8/2010 | Shelton, IV et al. | |
| 7,770,773 B2 | 8/2010 | Whitman et al. | |
| 7,770,775 B2 | 8/2010 | Shelton et al. | |
| 7,793,812 B2 | 9/2010 | Moore et al. | |
| 7,799,039 B2 | 9/2010 | Shelton, IV et al. | |
| 7,802,712 B2 | 9/2010 | Milliman et al. | |
| 7,803,151 B2 | 9/2010 | Whitman | |
| 7,819,896 B2 | 10/2010 | Racenet | |
| 7,822,458 B2 | 10/2010 | Webster, III et al. | |
| 7,845,534 B2 | 12/2010 | Viola et al. | |
| 7,845,537 B2 | 12/2010 | Shelton, IV et al. | |
| 7,857,185 B2 | 12/2010 | Swayze et al. | |
| 7,870,989 B2 | 1/2011 | Viola et al. | |
| 7,905,897 B2 | 3/2011 | Whitman et al. | |
| 7,918,230 B2 | 4/2011 | Whitman et al. | |
| 7,922,061 B2 | 4/2011 | Shelton, IV et al. | |
| 7,922,719 B2 | 4/2011 | Ralph et al. | |
| 7,947,034 B2 | 5/2011 | Whitman | |
| 7,951,071 B2 | 5/2011 | Whitman et al. | |
| 7,954,682 B2 | 6/2011 | Giordano et al. | |
| 7,959,051 B2 | 6/2011 | Smith et al. | |
| 7,963,433 B2 | 6/2011 | Whitman et al. | |
| 7,967,178 B2 | 6/2011 | Scirica et al. | |
| 7,967,179 B2 | 6/2011 | Olson et al. | |
| 7,992,758 B2 | 8/2011 | Whitman et al. | |
| 8,016,178 B2 | 9/2011 | Olson et al. | |
| 8,016,855 B2 | 9/2011 | Whitman et al. | |
| 8,020,743 B2 | 9/2011 | Shelton, IV | |
| 8,025,199 B2 | 9/2011 | Whitman et al. | |
| 8,035,487 B2 | 10/2011 | Malackowski | |
| 8,052,024 B2 | 11/2011 | Viola et al. | |
| 8,056,787 B2 | 11/2011 | Boudreaux et al. | |
| 8,114,118 B2 | 2/2012 | Knodel et al. | |
| 8,132,705 B2 | 3/2012 | Viola et al. | |
| 8,152,516 B2 | 4/2012 | Harvey et al. | |
| 8,157,150 B2 | 4/2012 | Viola et al. | |
| 8,157,151 B2 | 4/2012 | Ingmanson et al. | |
| 8,182,494 B1 | 5/2012 | Yencho et al. | |
| 8,186,555 B2 | 5/2012 | Shelton, IV et al. | |
| 8,186,587 B2 | 5/2012 | Zmood et al. | |
| 8,220,367 B2 | 7/2012 | Hsu | |
| 8,235,273 B2 | 8/2012 | Olson et al. | |
| 8,241,322 B2 | 8/2012 | Whitman et al. | |
| 8,272,554 B2 | 9/2012 | Whitman et al. | |
| 8,292,150 B2 | 10/2012 | Bryant | |
| 8,292,888 B2 | 10/2012 | Whitman | |
| 8,303,581 B2 | 11/2012 | Arts et al. | |
| 8,342,379 B2 | 1/2013 | Whitman et al. | |
| 8,348,855 B2 | 1/2013 | Hillely et al. | |
| 8,353,440 B2 | 1/2013 | Whitman et al. | |
| 8,357,144 B2 | 1/2013 | Whitman et al. | |
| 8,365,633 B2 | 2/2013 | Simaan et al. | |
| 8,365,972 B2 | 2/2013 | Aranyi | |
| 8,371,492 B2 | 2/2013 | Aranyi et al. | |
| 8,372,057 B2 | 2/2013 | Cude et al. | |
| 8,391,957 B2 | 3/2013 | Carlson et al. | |
| 8,424,739 B2 | 4/2013 | Racenet et al. | |
| 8,454,585 B2 | 6/2013 | Whitman | |
| 8,505,802 B2 | 8/2013 | Viola et al. | |
| 8,517,241 B2 | 8/2013 | Nicholas et al. | |
| 8,551,076 B2 | 10/2013 | Duval et al. | |
| 8,561,871 B2 | 10/2013 | Rajappa et al. | |
| 8,623,000 B2 | 1/2014 | Humayun et al. | |
| 8,632,463 B2 | 1/2014 | Drinan et al. | |
| 8,647,258 B2 | 2/2014 | Aranyi et al. | |
| 8,657,174 B2 | 2/2014 | Yates et al. | |
| 8,696,552 B2 | 4/2014 | Whitman | |
| 8,708,213 B2 | 4/2014 | Shelton, IV et al. | |
| 8,752,749 B2 | 6/2014 | Moore et al. | |
| 8,758,391 B2 | 6/2014 | Swayze et al. | |
| 8,806,973 B2 | 8/2014 | Ross et al. | |
| 8,851,355 B2 | 10/2014 | Aranyi et al. | |
| 8,858,571 B2 | 10/2014 | Shelton, IV et al. | |
| 8,875,972 B2 | 11/2014 | Weisenburgh, II et al. | |
| 8,893,946 B2 | 11/2014 | Boudreaux et al. | |
| 8,899,462 B2 | 12/2014 | Kostrzewski et al. | |
| 8,939,344 B2 | 1/2015 | Olson et al. | |
| 8,960,519 B2 | 2/2015 | Whitman et al. | |
| 8,961,396 B2 | 2/2015 | Azarbarzin et al. | |
| 8,967,443 B2 | 3/2015 | McCuen | |
| 8,968,276 B2 | 3/2015 | Zemlok et al. | |
| 8,968,337 B2 | 3/2015 | Whitfield et al. | |
| 8,992,422 B2 | 3/2015 | Spivey et al. | |
| 9,064,653 B2 | 6/2015 | Prest et al. | |
| 9,113,875 B2 | 8/2015 | Viola et al. | |
| 9,216,013 B2 | 12/2015 | Scirica et al. | |
| 9,282,961 B2 | 3/2016 | Whitman et al. | |
| 9,282,963 B2 | 3/2016 | Bryant | |
| 9,295,522 B2 | 3/2016 | Kostrzewski | |
| 9,307,986 B2 | 4/2016 | Hall et al. | |
| 2002/0049454 A1 | 4/2002 | Whitman et al. | |
| 2002/0165541 A1 | 11/2002 | Whitman | |
| 2003/0038938 A1 | 2/2003 | Jung et al. | |
| 2003/0165794 A1 | 9/2003 | Matoba | |
| 2004/0111012 A1 | 6/2004 | Whitman | |
| 2004/0133189 A1 | 7/2004 | Sakurai | |
| 2004/0176751 A1 | 9/2004 | Weitzner et al. | |
| 2005/0131442 A1 | 6/2005 | Yachia et al. | |
| 2006/0142656 A1 | 6/2006 | Malackowski et al. | |
| 2006/0142740 A1 | 6/2006 | Sherman et al. | |
| 2006/0278680 A1 | 12/2006 | Viola et al. | |
| 2007/0023476 A1 | 2/2007 | Whitman et al. | |
| 2007/0023477 A1 | 2/2007 | Whitman et al. | |
| 2007/0029363 A1 | 2/2007 | Popov | |
| 2007/0055219 A1 | 3/2007 | Whitman et al. | |
| 2007/0084897 A1 | 4/2007 | Shelton, IV et al. | |
| 2007/0102472 A1 | 5/2007 | Shelton, IV | |
| 2007/0152014 A1 | 7/2007 | Gillum et al. | |
| 2007/0175949 A1 | 8/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175955 A1 | 8/2007 | Shelton, IV et al. | |
| 2007/0175961 A1 | 8/2007 | Shelton et al. | |
| 2008/0029570 A1 | 2/2008 | Shelton, IV et al. | |
| 2008/0029573 A1 | 2/2008 | Shelton, IV et al. | |
| 2008/0029574 A1 | 2/2008 | Shelton, IV et al. | |
| 2008/0029575 A1 | 2/2008 | Shelton, IV et al. | |
| 2008/0058801 A1 | 3/2008 | Taylor et al. | |

(56) References Cited

U.S. PATENT DOCUMENTS

| | | | |
|---|---|---|---|
| 2008/0097487 A1* | 4/2008 | Pool | A61F 5/003 606/151 |
| 2008/0109012 A1 | 5/2008 | Falco et al. | |
| 2008/0110958 A1 | 5/2008 | McKenna et al. | |
| 2008/0167736 A1 | 7/2008 | Swayze et al. | |
| 2008/0185419 A1 | 8/2008 | Smith et al. | |
| 2008/0188841 A1 | 8/2008 | Tomasello et al. | |
| 2008/0197167 A1 | 8/2008 | Viola et al. | |
| 2008/0208195 A1 | 8/2008 | Shores et al. | |
| 2008/0237296 A1 | 10/2008 | Boudreaux et al. | |
| 2008/0251561 A1 | 10/2008 | Eades et al. | |
| 2008/0255413 A1 | 10/2008 | Zemlok et al. | |
| 2008/0255607 A1 | 10/2008 | Zemlok | |
| 2008/0262654 A1 | 10/2008 | Omori et al. | |
| 2008/0308603 A1 | 12/2008 | Shelton et al. | |
| 2009/0090763 A1 | 4/2009 | Zemlok et al. | |
| 2009/0099876 A1 | 4/2009 | Whitman | |
| 2009/0171147 A1 | 7/2009 | Lee et al. | |
| 2009/0182193 A1 | 7/2009 | Whitman et al. | |
| 2009/0209990 A1 | 8/2009 | Yates et al. | |
| 2009/0254094 A1 | 10/2009 | Knapp et al. | |
| 2010/0069942 A1 | 3/2010 | Shelton, IV | |
| 2010/0193568 A1 | 8/2010 | Scheib et al. | |
| 2010/0211053 A1 | 8/2010 | Ross et al. | |
| 2010/0225073 A1 | 9/2010 | Porter et al. | |
| 2011/0006101 A1 | 1/2011 | Hall et al. | |
| 2011/0017801 A1 | 1/2011 | Zemlok et al. | |
| 2011/0071508 A1 | 3/2011 | Duval et al. | |
| 2011/0077673 A1 | 3/2011 | Grubac et al. | |
| 2011/0121049 A1 | 5/2011 | Malinouskas et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174099 A1 | 7/2011 | Ross et al. | |
| 2011/0204119 A1 | 8/2011 | McCuen | |
| 2011/0218522 A1 | 9/2011 | Whitman | |
| 2011/0253765 A1 | 10/2011 | Nicholas et al. | |
| 2011/0276057 A1 | 11/2011 | Conlon et al. | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0074199 A1 | 3/2012 | Olson et al. | |
| 2012/0089131 A1 | 4/2012 | Zemlok et al. | |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0172924 A1 | 7/2012 | Allen, IV | |
| 2012/0223121 A1 | 9/2012 | Viola et al. | |
| 2012/0245428 A1 | 9/2012 | Smith et al. | |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2012/0330285 A1 | 12/2012 | Hartoumbekis et al. | |
| 2013/0018361 A1 | 1/2013 | Bryant | |
| 2013/0093149 A1 | 4/2013 | Saur et al. | |
| 2013/0098966 A1 | 4/2013 | Kostrzewski et al. | |
| 2013/0098968 A1 | 4/2013 | Aranyi et al. | |
| 2013/0098969 A1 | 4/2013 | Scirica et al. | |
| 2013/0181035 A1 | 7/2013 | Milliman | |
| 2013/0184704 A1 | 7/2013 | Beardsley et al. | |
| 2013/0214025 A1 | 8/2013 | Zemlok et al. | |
| 2013/0240596 A1 | 9/2013 | Whitman | |
| 2013/0274722 A1 | 10/2013 | Kostrzewski et al. | |
| 2013/0282052 A1 | 10/2013 | Aranyi et al. | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2014/0110455 A1 | 4/2014 | Ingmanson et al. | |
| 2014/0207125 A1 | 7/2014 | Applegate et al. | |
| 2014/0207182 A1 | 7/2014 | Zergiebel et al. | |
| 2014/0236173 A1 | 8/2014 | Scirica et al. | |
| 2014/0236174 A1 | 8/2014 | Williams et al. | |
| 2014/0276932 A1 | 9/2014 | Williams et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2014/0361068 A1 | 12/2014 | Aranyi et al. | |
| 2014/0373652 A1 | 12/2014 | Zergiebel et al. | |
| 2015/0048144 A1 | 2/2015 | Whitman | |
| 2015/0076205 A1 | 3/2015 | Zergiebel | |
| 2015/0080912 A1 | 3/2015 | Sapre | |
| 2015/0157321 A1 | 6/2015 | Zergiebel et al. | |
| 2015/0164502 A1 | 6/2015 | Richard et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |

FOREIGN PATENT DOCUMENTS

| | | |
|---|---|---|
| CN | 101856251 A | 10/2010 |
| CN | 102113902 A | 7/2011 |
| CN | 102247182 A | 11/2011 |
| DE | 102008053842 A1 | 5/2010 |
| EP | 0634144 | 1/1995 |
| EP | 0648476 A1 | 4/1995 |
| EP | 0686374 A2 | 12/1995 |
| EP | 0705571 A1 | 4/1996 |
| EP | 1690502 | 8/2006 |
| EP | 1723913 A1 | 11/2006 |
| EP | 1736112 | 12/2006 |
| EP | 1759652 A2 | 3/2007 |
| EP | 1769754 | 4/2007 |
| EP | 1772105 A1 | 4/2007 |
| EP | 1813199 A1 | 8/2007 |
| EP | 1813203 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 | 7/2008 |
| EP | 1943976 | 7/2008 |
| EP | 1952769 A2 | 8/2008 |
| EP | 2005898 A2 | 12/2008 |
| EP | 2027819 | 2/2009 |
| EP | 2044890 A1 | 4/2009 |
| EP | 2055243 | 5/2009 |
| EP | 2090247 A1 | 8/2009 |
| EP | 2098170 | 9/2009 |
| EP | 2100561 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2 606 834 | 6/2013 |

(56) References Cited

FOREIGN PATENT DOCUMENTS

| EP | 2606834 A2 | 6/2013 |
|---|---|---|
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08-038488 | 2/1996 |
| JP | 2005-125075 A | 5/2005 |
| JP | 2011-115594 A | 6/2011 |
| KR | 20120022521 A | 3/2012 |
| WO | 99/15086 A1 | 4/1999 |
| WO | WO 00/72760 | 12/2000 |
| WO | WO 00/72765 | 12/2000 |
| WO | 03/000138 A2 | 1/2003 |
| WO | 03/030743 A2 | 4/2003 |
| WO | WO 03/026511 | 4/2003 |
| WO | 03065916 A1 | 8/2003 |
| WO | WO 03/077769 | 9/2003 |
| WO | 03090630 A2 | 11/2003 |
| WO | WO 2004/107989 | 12/2004 |
| WO | WO 2006/042210 | 4/2006 |
| WO | 2007016290 A2 | 2/2007 |
| WO | WO 2007/014355 | 2/2007 |
| WO | WO 2007/026354 | 3/2007 |
| WO | 2007137304 A2 | 11/2007 |
| WO | WO 2008/131362 | 10/2008 |
| WO | WO 2008/133956 | 11/2008 |
| WO | WO 2009/039506 | 3/2009 |
| WO | WO 2009/132359 | 10/2009 |
| WO | 2009/143092 A1 | 11/2009 |
| WO | 2009149234 A1 | 12/2009 |
| WO | 2011/108840 A2 | 9/2011 |
| WO | 2012040984 A1 | 4/2012 |

OTHER PUBLICATIONS

Chinese Office Action issued in Appl. No. CN 201310284898.5 dated Jul. 26, 2016.
Extended European Search Report dated Sep. 14, 2015, corresponding to European Patent Application No. 15169962.6; 7 pages.
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
International Search Report corresponding to PCT/US2005/027266, completed May 30, 2008 and dated Jun. 18, 2008; (2 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
Extended European Search Report corresponding to EP 08 25 2703.7, completed Oct. 23, 2008 and dated Oct. 31, 2008; (7 pp.).
Extended European Search Report corresponding to EP 13 17 5475.6, completed Sep. 23, 2013 and dated Oct. 1, 2013; (8 pp).
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15, 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.

(56) References Cited

OTHER PUBLICATIONS

Extended European Search Report corresponding to International Application No. EP 15 18 8539.9 dated Feb. 17 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action (with English translation), dated Feb. 21, 2017, corresponding to Chinese Application No. 201310284898.5; 9 total pages.
Japanese Office Action (with English translation), dated Mar. 29, 2017, corresponding to Japanese Application No. 2013-137994; 18 total pages.

\* cited by examiner

SURGICAL ADAPTER ASSEMBLIES FOR USE BETWEEN SURGICAL HANDLE ASSEMBLY AND SURGICAL END EFFECTORS

CROSS REFERENCE TO RELATED APPLICATION

The present application claims the benefit of and priority to U.S. Provisional Application Ser. No. 61/669,208, filed on Jul. 9, 2012, the entire contents of which are incorporated herein by reference.

BACKGROUND

1. Technical Field

The present disclosure relates to surgical devices. More specifically, the present disclosure relates to surgical adapters and/or adapter assemblies for use between and for interconnecting a powered, rotating and/or articulating surgical device or handle assembly and an end effector for clamping, cutting and/or stapling tissue.

2. Background of Related Art

One type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary powered drive systems for operating and/or manipulating the surgical device. In many instances the surgical devices include a powered handle assembly, which is reusable, and a disposable end effector or the like that is selectively connected to the powered handle assembly prior to use and then disconnected from the end effector following use in order to be disposed of or in some instances sterilized for re-use.

Many of the existing end effectors for use with many of the existing powered surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with powered surgical devices and/or handle assemblies that use a rotary motion to deliver power, a need exists for adapters and/or adapter assemblies to interface between and interconnect the linear driven end effectors with the powered rotary driven surgical devices and/or handle assemblies.

These adapters and/or adapter assemblies must be able to convert rotation of a rotatable drive screw to linear motion of a drive rod or the like. Such force conversion creates a relatively high degree of strain on the system at the force conversion interface. Additionally, these adapters and/or adapter assemblies must undergo several autoclaving cycles without deterioration of the system at the force conversion interface.

Accordingly, a need exists for adapters and/or adapter assemblies constructed from materials that are biocompatible, which are resistant to corrosion from steam and cleaning agents, and which have a relatively high fatigue lifecycle.

SUMMARY

The present disclosure relates to surgical adapters and/or adapter assemblies for use between and for interconnecting a powered, rotating and/or articulating surgical device or handle assembly and an end effector for clamping, cutting and/or stapling tissue.

According to an aspect of the present disclosure, an adapter assembly is provided for selectively interconnecting a surgical end effector that is configured to perform a function and a surgical device that is configured to actuate the end effector, the end effector including at least one axially translatable drive member, and the surgical device including at least one rotatable drive shaft.

The adapter assembly includes at least one drive converter assembly for interconnecting a respective one of the at least one rotatable drive shaft of the surgical device and one of the at least one axially translatable drive member of the end effector, wherein the at least one drive converter assembly includes a first end that is connectable to a first rotatable drive shaft of the surgical device and a second end that is connectable to a first axially translatable drive member of the end effector, wherein the at least one drive converter assembly converts and transmits a rotation of the first rotatable drive shaft of the surgical device to an axial translation of the first axially translatable drive member of the end effector.

The at least one drive converter assembly includes a drive shaft rotatably disposed within the housing and the outer tube, wherein a proximal end of the drive shaft of the at least one drive converter assembly is in operative communication with the coupling sleeve, wherein the drive shaft of the at least one drive converter assembly has a threaded distal end portion; a drive coupling nut threadably connected to the distal end portion of the drive shaft of the at least one drive converter assembly, wherein the drive coupling nut is inhibited from axial rotation relative to the drive shaft of the at least one drive converter assembly; and an axially translatable drive bar having a proximal portion connected to the drive coupling nut and a distal portion configured and adapted for selective connection to an axially translatable drive member of the end effector.

In use, rotation of the first rotatable drive shaft of the surgical device results in rotation of the drive shaft of the at least one drive converter assembly, and wherein rotation of the drive shaft of the at least one drive converter assembly results in axial translation of the drive coupling nut and the drive bar that is connected thereto.

The drive coupling nut of the at least one drive converter assembly may engage 25-36 teeth (e.g., turns of a thread forming the threaded distal end portion of the drive shaft), preferably 29 teeth or turns, of the threaded distal end portion of the drive shaft.

The drive coupling nut of the at least one drive converter assembly may be manufactured from unreinforced polyetheretherketone (PEEK) thermoplastic polymer.

The threaded distal end portion of the drive shaft of the at least one drive converter assembly may be configured as a Unified-series thread profile (UNC #4-48 class 3A).

The threaded distal end portion of the drive shaft of the at least one drive converter assembly is processed by surface hardening, rolling, whirling and/or electro-polishing.

The at least one drive converter assembly may include a first washer disposed adjacent a proximal surface of the drive coupling nut, and a second washer disposed against a distal surface of the drive coupling nut.

The drive coupling nut of the at least one drive converter assembly may include at least one outer annular rib.

The adapter assembly may further include a housing configured and adapted for connection with the surgical device and to be in operative communication with each of the at least one rotatable drive shaft of the surgical device.

The adapter assembly may further include an outer tube having a proximal end supported by the housing and a distal end configured and adapted for connection with the end effector, wherein the distal end of the outer tube is in operative communication with each of the at least one axially translatable drive member of the end effector.

According to another aspect of the present disclosure, a method of fabricating an adapter assembly is provided, wherein the adapter assembly selectively interconnects a surgical end effector and a surgical device. The method includes the steps of providing a drive coupling nut constructed from unreinforced polyetheretherketone (PEEK) thermoplastic polymer; and providing a drive shaft including a proximal end configured to receive a rotation from a rotatable drive shaft of the surgical device. The drive shaft fabrication including the steps of surface hardening at least a distal end of the drive shaft; after surface hardening the distal end of the drive shaft, whirling the distal end of the drive shaft; and after whirling the distal end of the drive shaft, electro-polishing the distal end of the drive shaft. The method of fabricating the adapter assembly further including the steps of providing a drive bar; securing the drive bar to the drive coupling nut; and threading the drive coupling nut to the threaded distal end of the drive shaft.

The assembled drive bar, drive coupling nut and drive shaft define a drive converter assembly configured to interconnect a rotatable drive shaft of the surgical device and an axially translatable drive member of the end effector, wherein the drive converter assembly converts and transmits a rotation of the first rotatable drive shaft of the surgical device to an axial translation of the first axially translatable drive member of the end effector.

In use, rotation of the first rotatable drive shaft of the surgical device results in rotation of the drive shaft of the at least one drive converter assembly, and wherein rotation of the drive shaft of the at least one drive converter assembly results in axial translation of the drive coupling nut and the drive bar that is connected thereto.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
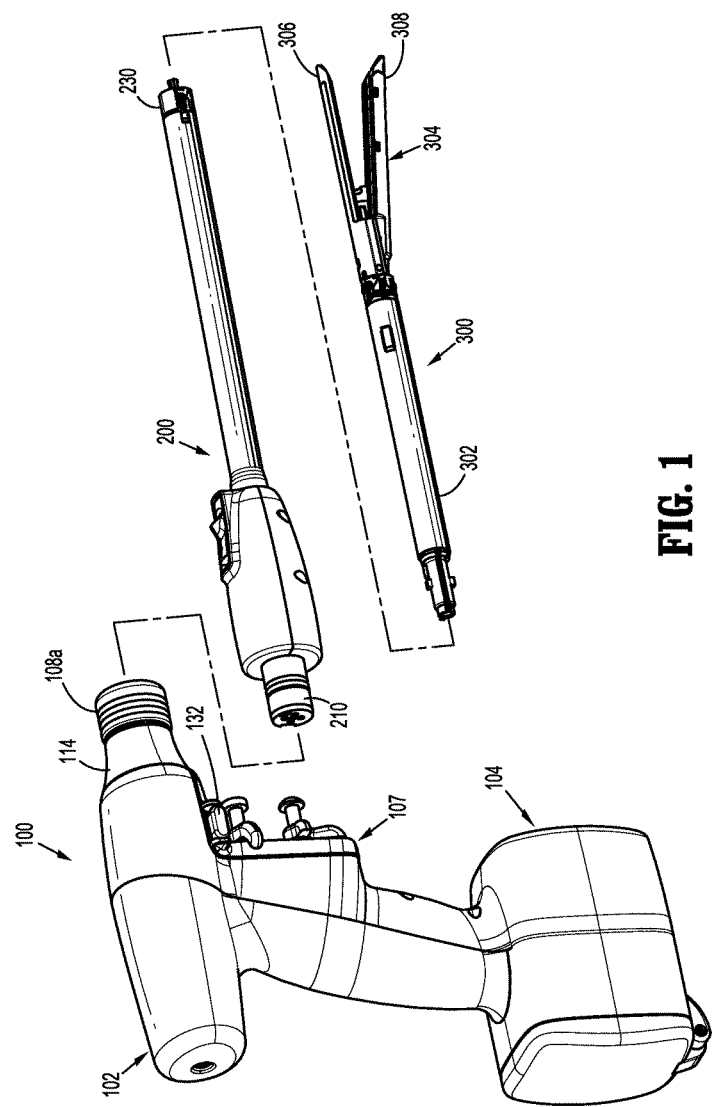
FIG. 1 is a perspective view, with parts separated, of a surgical device and adapter assembly, in accordance with an embodiment of the present disclosure, illustrating a connection thereof with an end effector.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical instrument configured for selective attachment thereto of a plurality of different end effectors that are each configured for actuation and manipulation by the powered hand held electromechanical surgical instrument.

As illustrated in FIG. 1, surgical device 100 is configured for selective connection with an adapter assembly 200, and, in turn, adapter assembly 200 is configured for selective connection with an end effector or single use loading unit 300.

Figure 2:
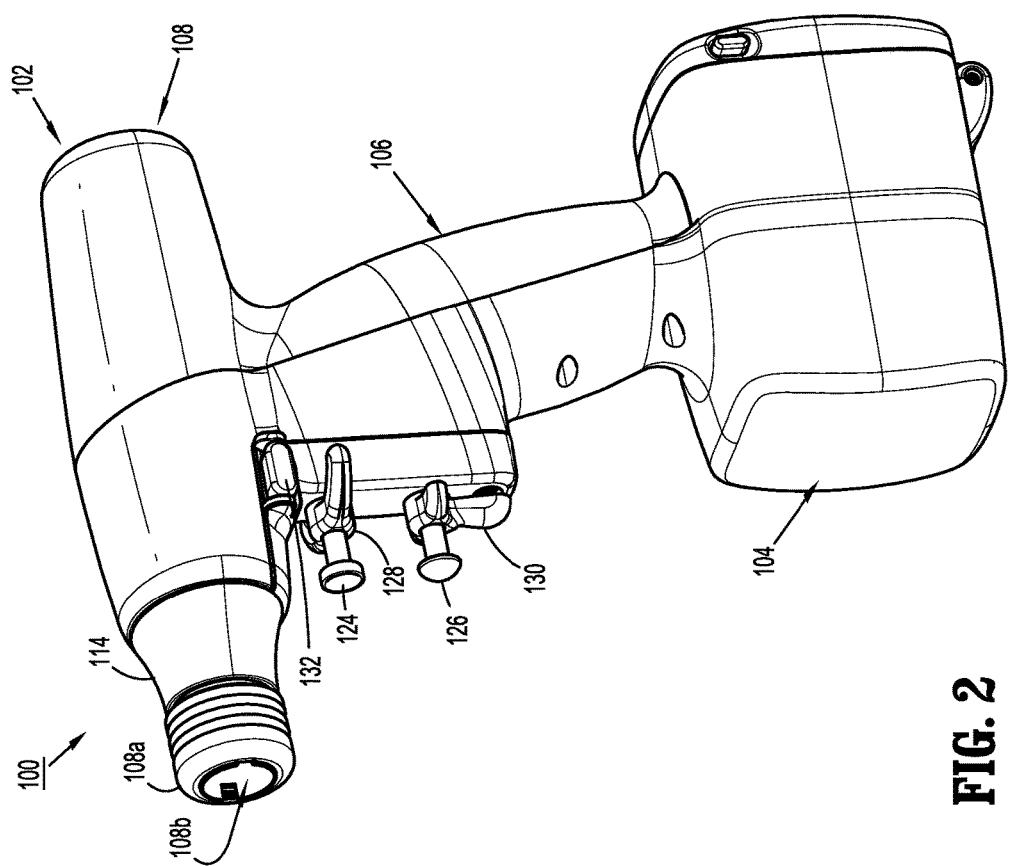
FIG. 2 is a perspective view of the surgical device of FIG. 1.

As illustrated in FIGS. 1 and 2, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section that is integrally formed with and extending from the lower portion 104, and a proximal half-section connectable to the distal half-section by a plurality of fasteners. When joined, the distal and proximal half-sections define a handle housing 102 having a cavity therein in which a circuit board (not shown) and a drive mechanism (not shown) is situated.

Figure 3:
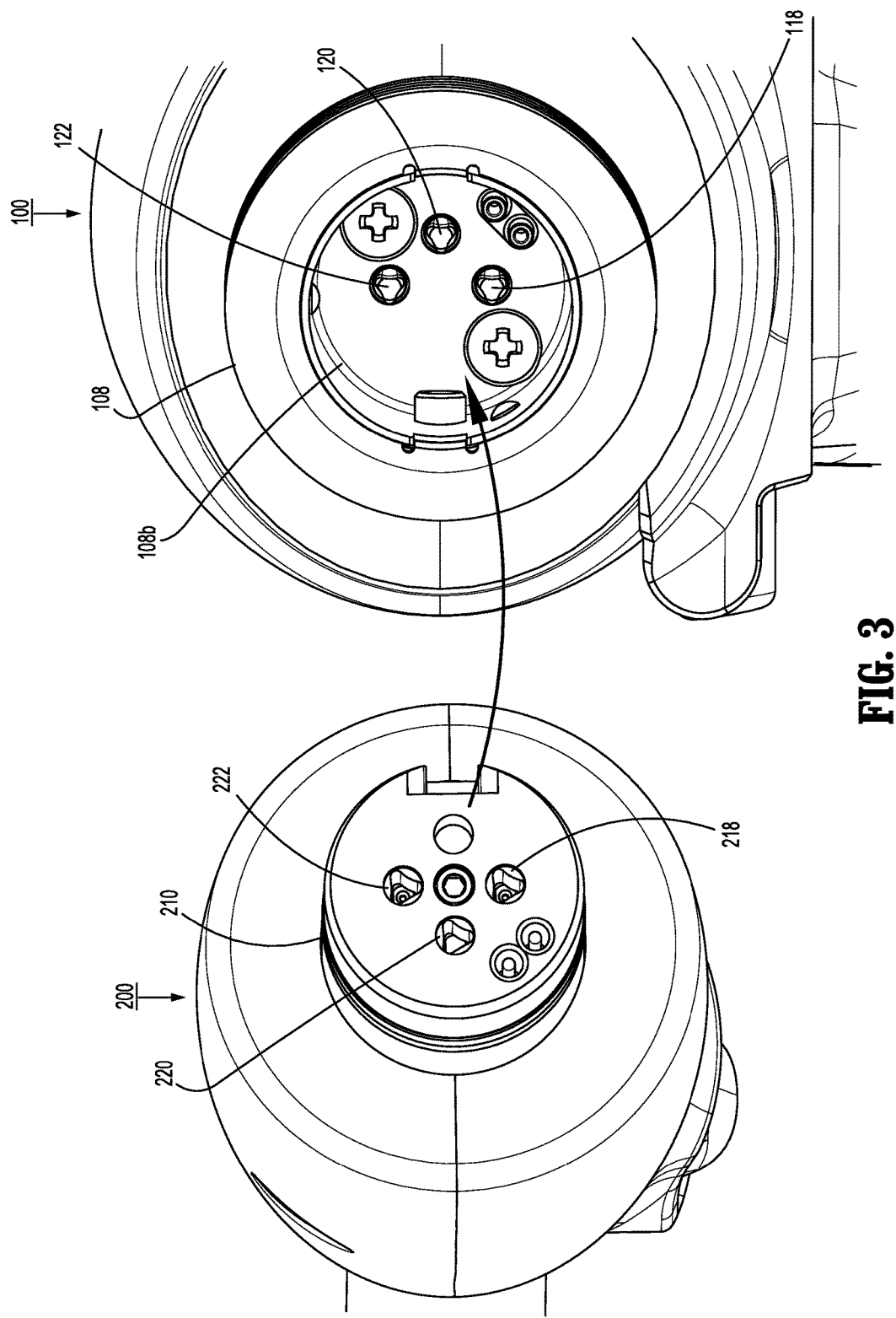
FIG. 3 is a perspective view of the connecting ends of each of the surgical device and the adapter assembly, illustrating a connection therebetween.

With reference to FIGS. 1-3, the distal half-section of upper housing portion 108 defines a nose or connecting portion 108a. A nose cone 114 is supported on nose portion 108a of upper housing portion 108. Nose cone 114 is fabricated from a transparent material. An illumination member (not shown) is disposed within nose cone 114 such that the illumination member is visible therethrough. The illumination member may be in the form of a light emitting diode printed circuit board (LED PCB). The illumination member may be configured to illuminate multiple colors with a specific color pattern being associated with a unique discrete event.

Figure 4:
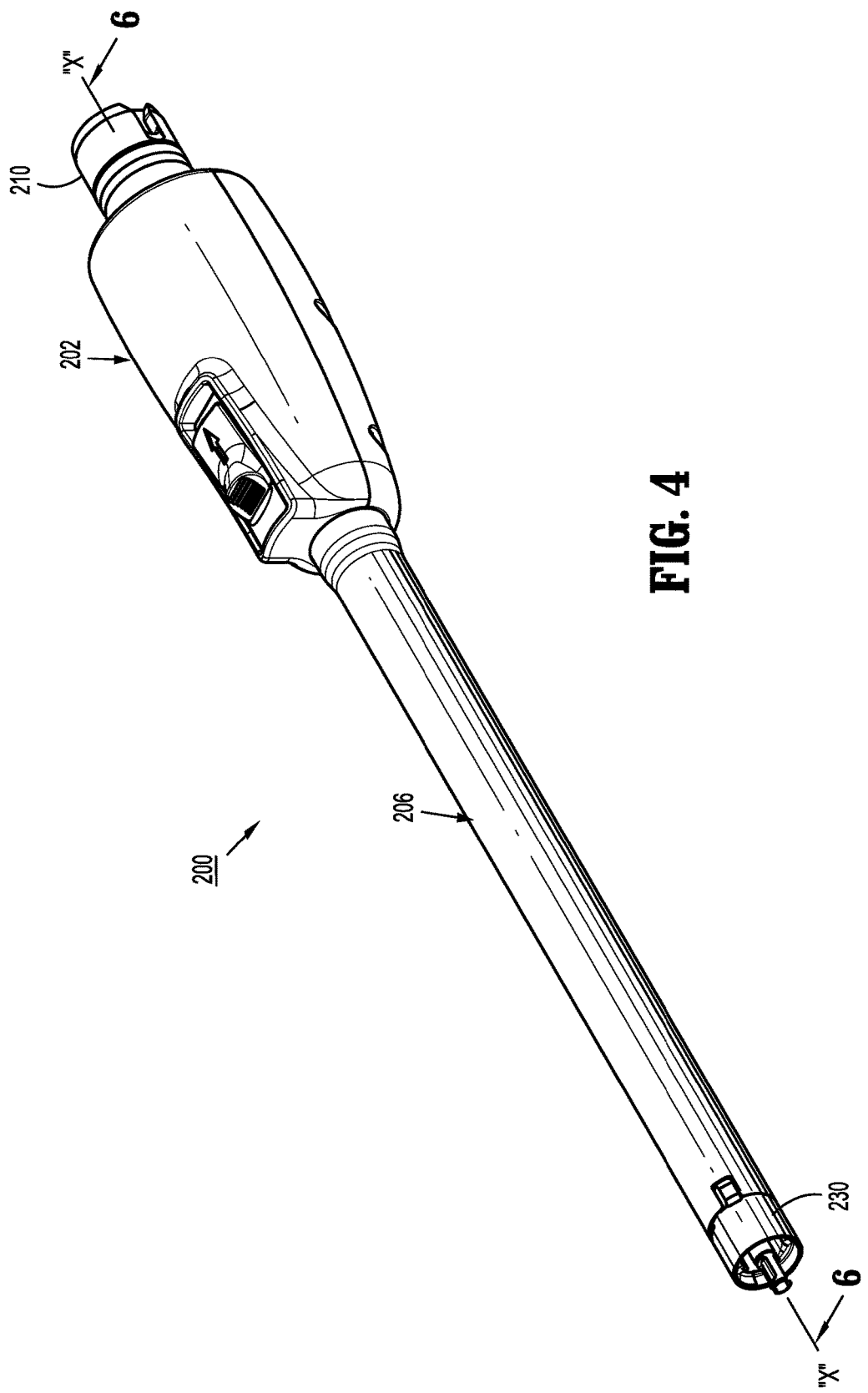
FIG. 4 is a perspective view of the adapter assembly of FIG. 1.
Figure 5:
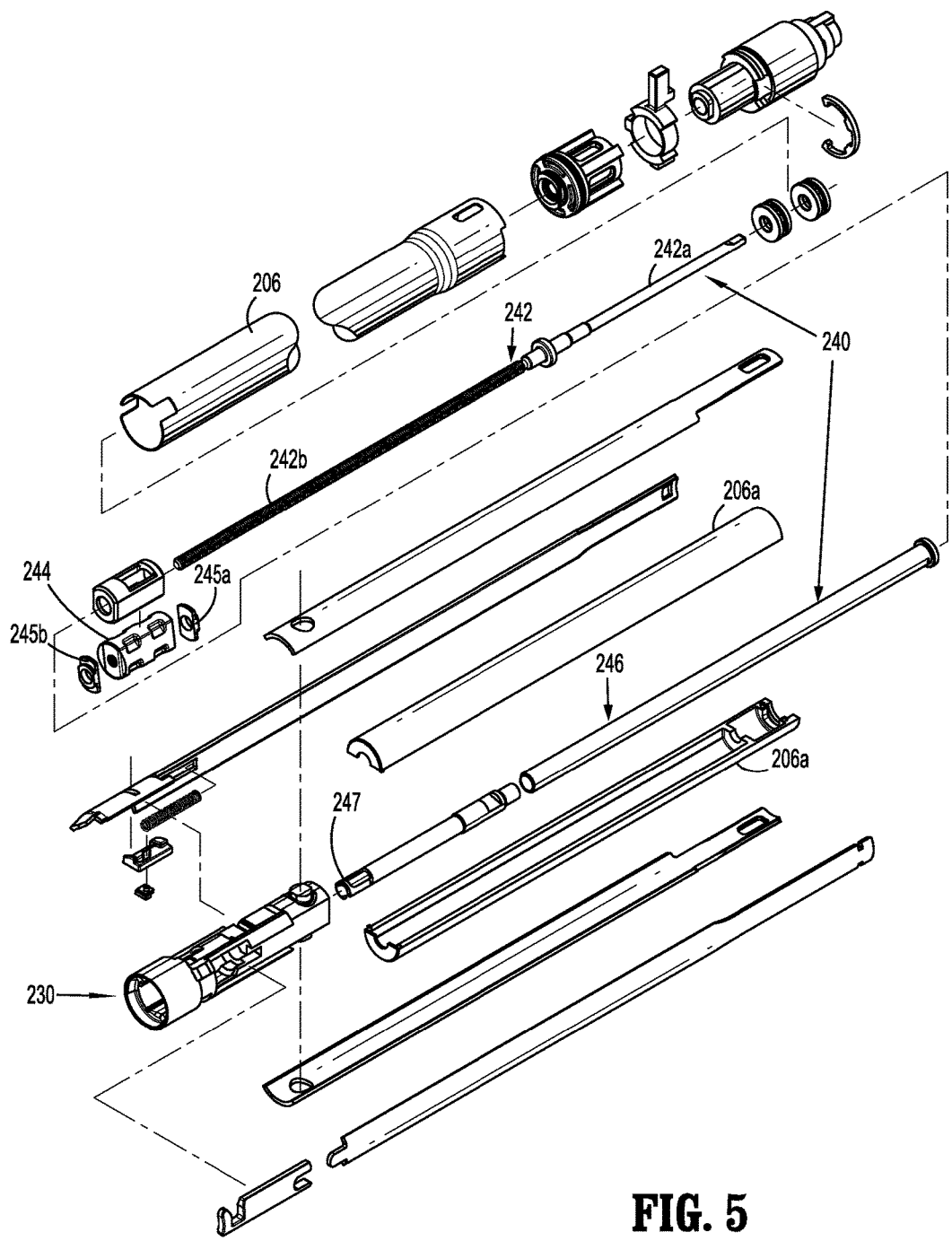
FIG. 5 is a perspective view, with parts separated, of the adapter assembly of FIGS. 1-4.

Upper housing portion 108 of handle housing 102 provides a housing in which the drive mechanism is situated. The drive mechanism is configured to drive shafts and/or gear components in order to perform the various operations of surgical device 100. In particular, the drive mechanism is configured to drive shafts and/or gear components in order to selectively move tool assembly 304 of end effector 300 (see FIGS. 1 and 8) relative to proximal body portion 302 of end effector 300, to rotate end effector 300 about a longitudinal axis "X" (see FIG. 4) relative to handle housing 102, to move anvil assembly 306 relative to cartridge assembly 308 of end effector 300, and/or to fire a stapling and cutting cartridge within cartridge assembly 308 of end effector 300.

As illustrated in FIGS. 1-3, and as mentioned above, the distal half-section of upper housing portion 108 defines a connecting portion 108a configured to accept a corresponding drive coupling assembly 210 of adapter assembly 200.

As illustrated in FIGS. 2 and 3, connecting portion 108a of surgical device 100 has a cylindrical recess 108b that receives a drive coupling assembly 210 of adapter assembly 200 when adapter assembly 200 is mated to surgical device 100. Connecting portion 108a houses three rotatable drive connectors 118, 120, 122.

When adapter assembly 200 is mated to surgical device 100, each of rotatable drive connectors 118, 120, 122 of surgical device 100 couples with a corresponding rotatable connector sleeve 218, 220, 222 of adapter assembly 200. (see FIG. 3). In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of adapter assembly 200.

The mating of drive connectors 118, 120, 122 of surgical device 100 with connector sleeves 218, 220, 222 of adapter assembly 200 allows rotational forces to be independently transmitted via each of the three respective connector interfaces. The drive connectors 118, 120, 122 of surgical device 100 are configured to be independently rotated by the drive mechanism. In this regard, a function selection module of the drive mechanism selects which drive connector or connectors 118, 120, 122 of surgical device 100 is to be driven by an input drive component of the drive mechanism.

Since each of drive connectors 118, 120, 122 of surgical device 100 has a keyed and/or substantially non-rotatable interface with respective connector sleeves 218, 220, 222 of adapter assembly 200, when adapter assembly 200 is coupled to surgical device 100, rotational force(s) are selectively transferred from the drive mechanism of surgical device 100 to adapter assembly 200.

The selective rotation of drive connector(s) 118, 120 and/or 122 of surgical device 100 allows surgical device 100 to selectively actuate different functions of end effector 300. As will be discussed in greater detail below, selective and independent rotation of first drive connector 118 of surgical device 100 corresponds to the selective and independent opening and closing of tool assembly 304 of end effector 300, and driving of a stapling/cutting component of tool assembly 304 of end effector 300. Also, the selective and independent rotation of second drive connector 120 of surgical device 100 corresponds to the selective and independent articulation of tool assembly 304 of end effector 300 transverse to longitudinal axis "X" (see FIG. 4). Additionally, the selective and independent rotation of third drive connector 122 of surgical device 100 corresponds to the selective and independent rotation of end effector 300 about longitudinal axis "X" (see FIG. 4) relative to handle housing 102 of surgical device 100.

As illustrated in FIGS. 1 and 2, handle housing 102 supports a pair of finger-actuated control buttons 124, 126 and rocker devices 128, 130.

Actuation of first control button 124 causes tool assembly 304 of end effector 300 to close and/or a stapling/cutting cartridge within tool assembly 304 of end effector 300 to fire.

Actuation of rocker device 128 in a first direction causes tool assembly 304 to articulate relative to body portion 302 in a first direction, while actuation of rocker device 128 in an opposite, e.g., second, direction causes tool assembly 304 to articulate relative to body portion 302 in an opposite, e.g., second, direction.

Actuation of control button 126 causes tool assembly 304 of end effector 300 to open.

Actuation of rocker device 130 causes end effector 300 to rotate relative to handle housing 102 of surgical device 100. Specifically, movement of rocker device 130 in a first direction causes end effector 300 to rotate relative to handle housing 102 in a first direction, while movement of rocker device 130 in an opposite, e.g., second, direction causes end effector 300 to rotate relative to handle housing 102 in an opposite, e.g., second, direction.

As illustrated in FIGS. 1-3, surgical device 100 is configured for selective connection with adapter assembly 200, and, in turn, adapter assembly 200 is configured for selective connection with end effector 300.

Figure 8:
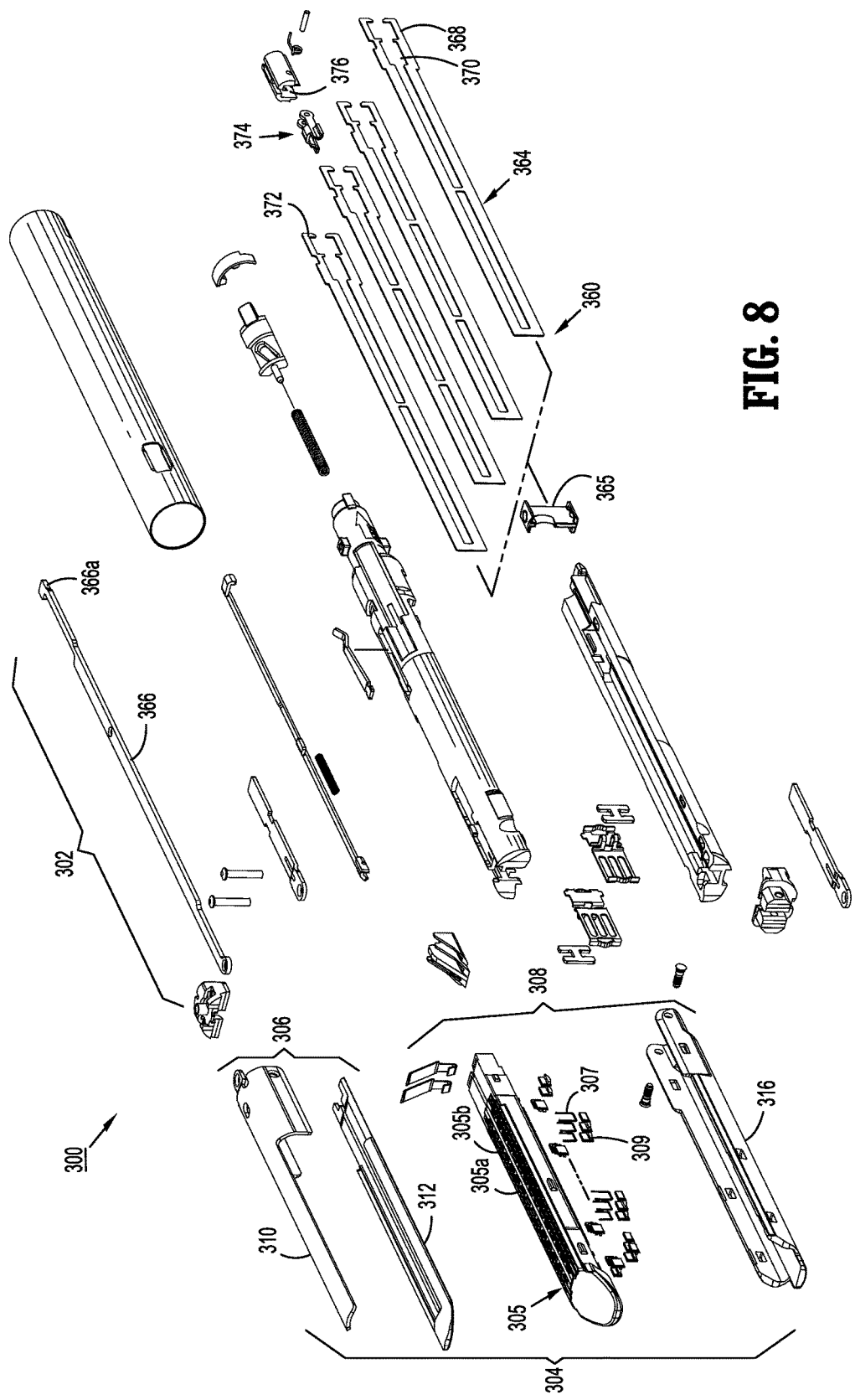
FIG. 8 is a perspective view, with parts separated, of an exemplary end effector for use with the surgical device and the adapter assembly of the present disclosure.

Adapter assembly 200 is configured to convert a rotation of either of drive connectors 120 and 122 of surgical device 100 into axial translation useful for operating a drive assembly 360 and an articulation link 366 of end effector 300, as illustrated in FIG. 8.

Adapter assembly 200 may include a first drive transmitting/converting assembly for interconnecting third rotatable drive connector 122 of surgical device 100 and a first axially translatable drive member of end effector 300, wherein the first drive transmitting/converting assembly converts and transmits a rotation of third rotatable drive connector 122 of surgical device 100 to an axial translation of the first axially translatable drive assembly 360 (see FIG. 8) of end effector 300 for firing.

Adapter assembly 200 may include a second drive transmitting/converting assembly for interconnecting second rotatable drive connector 120 of surgical device 100 and a second axially translatable drive member of end effector 300, wherein the second drive transmitting/converting assembly converts and transmits a rotation of second rotatable drive connector 120 of surgical device 100 to an axial translation of articulation link 366 (see FIG. 8) of end effector 300 for articulation.

Turning now to FIGS. 4-7, adapter assembly 200 includes a knob housing 202 and an outer tube 206 extending from a distal end of knob housing 202. Knob housing 202 and outer tube 206 are configured and dimensioned to house the components of adapter assembly 200. Outer tube 206 is dimensioned for endoscopic insertion, in particular, that outer tube is passable through a typical trocar port, cannula or the like. Knob housing 202 is dimensioned to not enter the trocar port, cannula of the like.

Knob housing 202 is configured and adapted to connect to connecting portion 108a of upper housing portion 108 of the distal half-section of surgical device 100.

As seen in FIGS. 4-7, adapter assembly 200 includes a surgical device drive coupling assembly 210 at a proximal end thereof and to an end effector coupling assembly 230 at a distal end thereof.

Adapter assembly 200 includes a first, a second and a third drive transmitting/converting assembly, as mentioned above, disposed within handle housing 202 and outer tube 206. Each drive transmitting/converting assembly is configured and adapted to transmit or convert a rotation of a first, second and third drive connector 118, 120, 122 of surgical device 100 into axial translation of a drive bar of adapter assembly 200, to effectuate closing, opening, articulating and firing of end effector 300; or a rotation of adapter assembly 200.

In particular, adapter assembly 200 includes a first drive transmitting/converting assembly 240 disposed within handle housing 202 and outer tube 206. Drive transmitting/converting assembly 240 is configured and adapted to transmit or convert a rotation of a first drive connector 118 of surgical device 100 into axial translation of a drive tube 246 of adapter 200, to effectuate closing, opening, articulating and firing of end effector 300.

As seen in FIGS. 4-7, first drive transmitting/converting assembly 240 includes a first distal drive shaft 242 rotatably supported within housing 202 and outer tube 206. A proximal end portion 242a of first distal drive shaft 242 is keyed to a spur gear 242c. First distal drive shaft 242 further includes a distal end portion 242b having a threaded outer profile or surface.

In accordance with the present disclosure, the threaded outer profile of distal end portion 242b of first distal drive shaft 242 may be configured as a Unified-series thread profile (UNC #4-48 class 3A). Additionally, in accordance with the present disclosure, the threaded outer profile of distal end portion 242b of first distal drive shaft 242 is fabricated by thread whirling or rolling to harden the surface, followed by secondary electro-polishing to smooth the surface. Electro-polishing of the threaded outer profile of distal end portion 242b of first distal drive shaft 242 functions to smooth the threads for interface with the PEEK material of drive coupling nut 244 to increase the wear resistance and the life therebetween.

First drive transmitting/converting assembly 240 further includes a drive coupling nut 244 rotatably coupled to threaded distal end portion 242b of first distal drive shaft 242. Drive coupling nut 244 is slidably disposed within inner housing tube 206a. Moreover, drive coupling nut 244 is keyed to inner housing tube 206a so as to be prevented from rotation as first distal drive shaft 242 is rotated. In this manner, as first distal drive shaft 242 is rotated, drive coupling nut 244 is translated through and/or along inner housing tube 206a.

Figure 6:
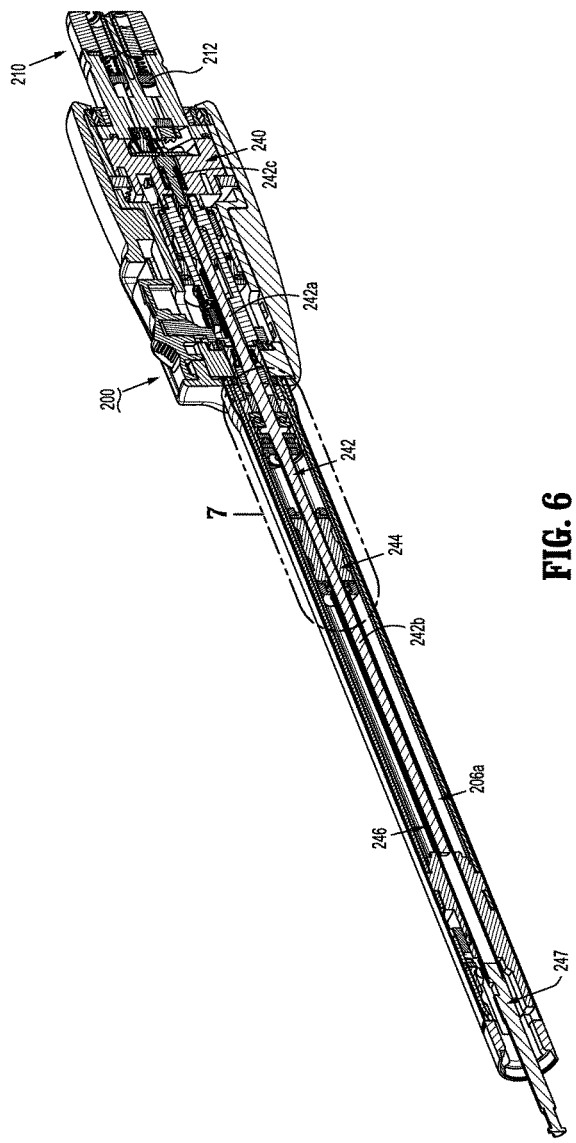
FIG. 6 is a cross-sectional view of the adapter assembly of FIGS. 1-5, as taken through 6-6 of FIG. 4.
Figure 7:
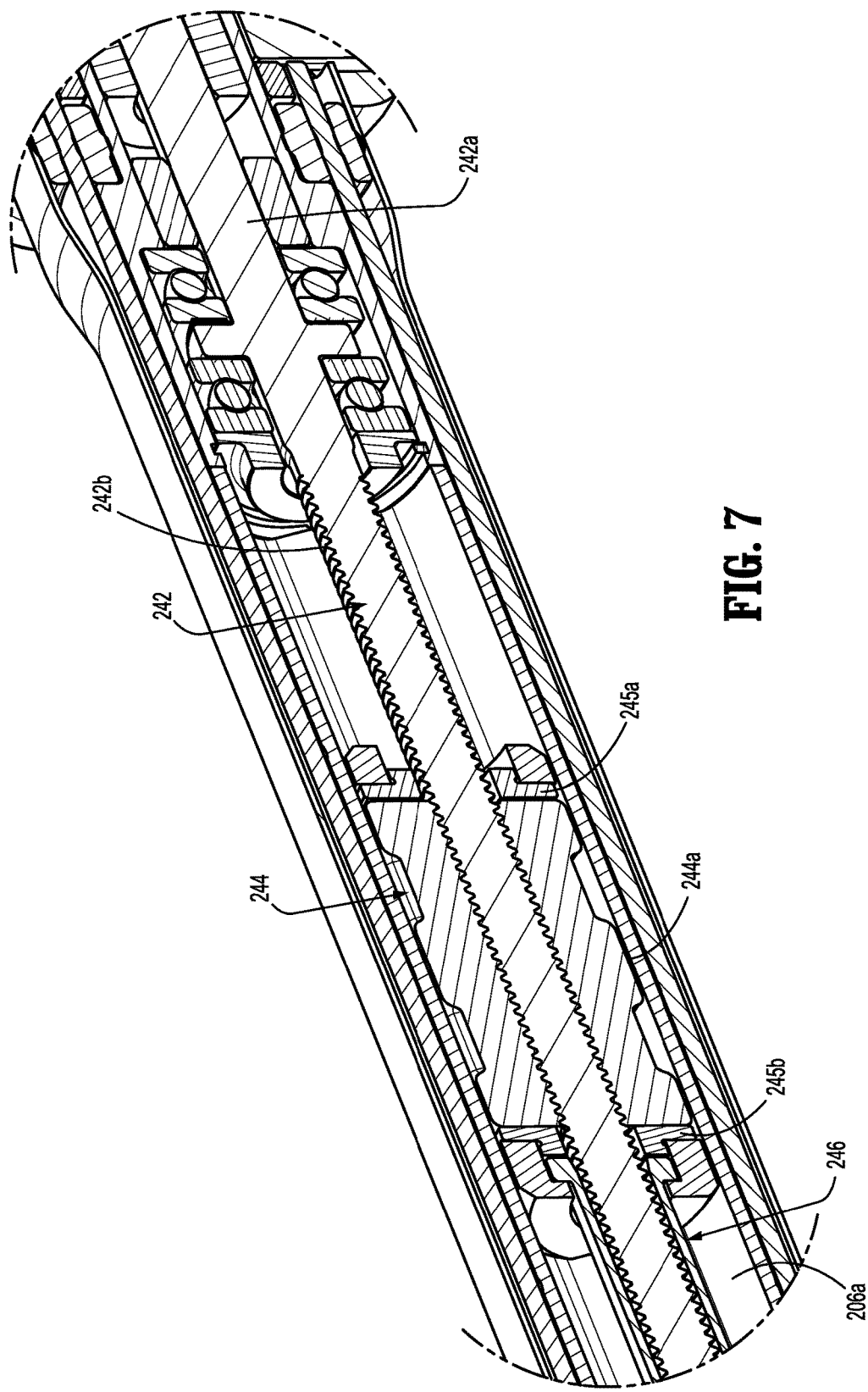
FIG. 7 is an enlarged, perspective view of the indicated area of detail of FIG. 6.

As seen in FIGS. 6 and 7, drive coupling nut 244 is supported at its proximal and distal ends by respective washers 245a, 245b. Washers 245a, 245b aid in distributing the loaded and aid in avoiding stress concentrations exerted on drive coupling nut 244 by threaded distal end portion 242b of first distal drive shaft 242, as first distal drive shaft 242 is rotated.

With continued reference to FIGS. 6 and 7, drive coupling nut 244 may be molded and may be provided with at least one outer annular rib 244a to help maintain a uniform wall thickness.

In order to achieve uniform pressure distribution along the thread of drive coupling nut 244, it is contemplated that drive coupling nut 244 be manufactured from unreinforced polyetheretherketone (PEEK) thermoplastic polymer. Unreinforced PEEK has a Modulus of Elasticity which is about 55 times lower than that of stainless steel. Additionally, an elongation of unreinforced PEEK, at yield, equals about 5% and an elongation of unreinforced PEEK, at break, equals about 45%. Stated differently, the material of drive coupling nut 244 is relatively soft and highly ductile, yet at the same time is relatively strong (i.e., having a yield strength equal to about 14,500 psi) and is highly resistant to autoclaving.

In accordance with the present disclosure, drive coupling nut 244 is dimensioned such that drive coupling nut 244 engages between 25-35 threads, preferably 29 threads, of threaded distal end portion 242b of first distal drive shaft 242.

In order to help with reducing friction and reducing heat build-up, a lubricant, such as, KRYTOX® 206, commercially available from DuPont™ (a grease compatible with PEEK and which can withstand the autoclaving process) may be applied to and/or between distal end portion 242b of first distal drive shaft 242 and drive coupling nut 244.

First drive transmitting/converting assembly 240 further includes a drive tube 246 surrounding first distal drive shaft 242 and having a proximal end portion connected to drive coupling nut 244 and a distal end portion extending beyond distal end portion 242b of first distal drive shaft 242. The distal end portion of drive tube 246 supports a connection member 247 configured and dimensioned for selective engagement with drive member 374 (see FIG. 8) of drive assembly 360 of end effector 300.

In operation, as first rotatable proximal drive shaft 212 is rotated, as a result of the rotation of the first respective drive connector 118 of surgical device 100, first rotatable proximal drive shaft 212 is rotated and transmits rotation to spur gear 242c, that is keyed to first distal drive shaft 242, to thereby cause rotation of first distal drive shaft 242. As first distal drive shaft 242 is rotated, drive coupling nut 244 is caused to be translated axially along first distal drive shaft 242.

As drive coupling nut 244 is caused to be translated axially along first distal drive shaft 242, drive tube 246 is caused to be translated axially relative to inner housing tube 206a of outer tube 206. As drive tube 246 is translated axially, with connection member 247 connected thereto and connected to a drive member 374 (see FIG. 8) of drive assembly 360 of end effector 300, drive tube 246 causes concomitant axial translation of drive member 374 of end effector 300 to effectuate a closure of tool assembly 304 and a firing of tool assembly 304 of end effector 300.

In operation, when a button of surgical device 100 is activated by the user, the software checks predefined conditions. If conditions are met, the software controls the motors and delivers mechanical drive to the attached surgical stapler, which can then open, close, rotate, articulate or fire depending on the function of the pressed button. The software also provides feedback to the user by turning colored lights on or off in a defined manner to indicate the status of surgical device 100, adapter assembly 200 and/or end effector 300.

Figure 9:
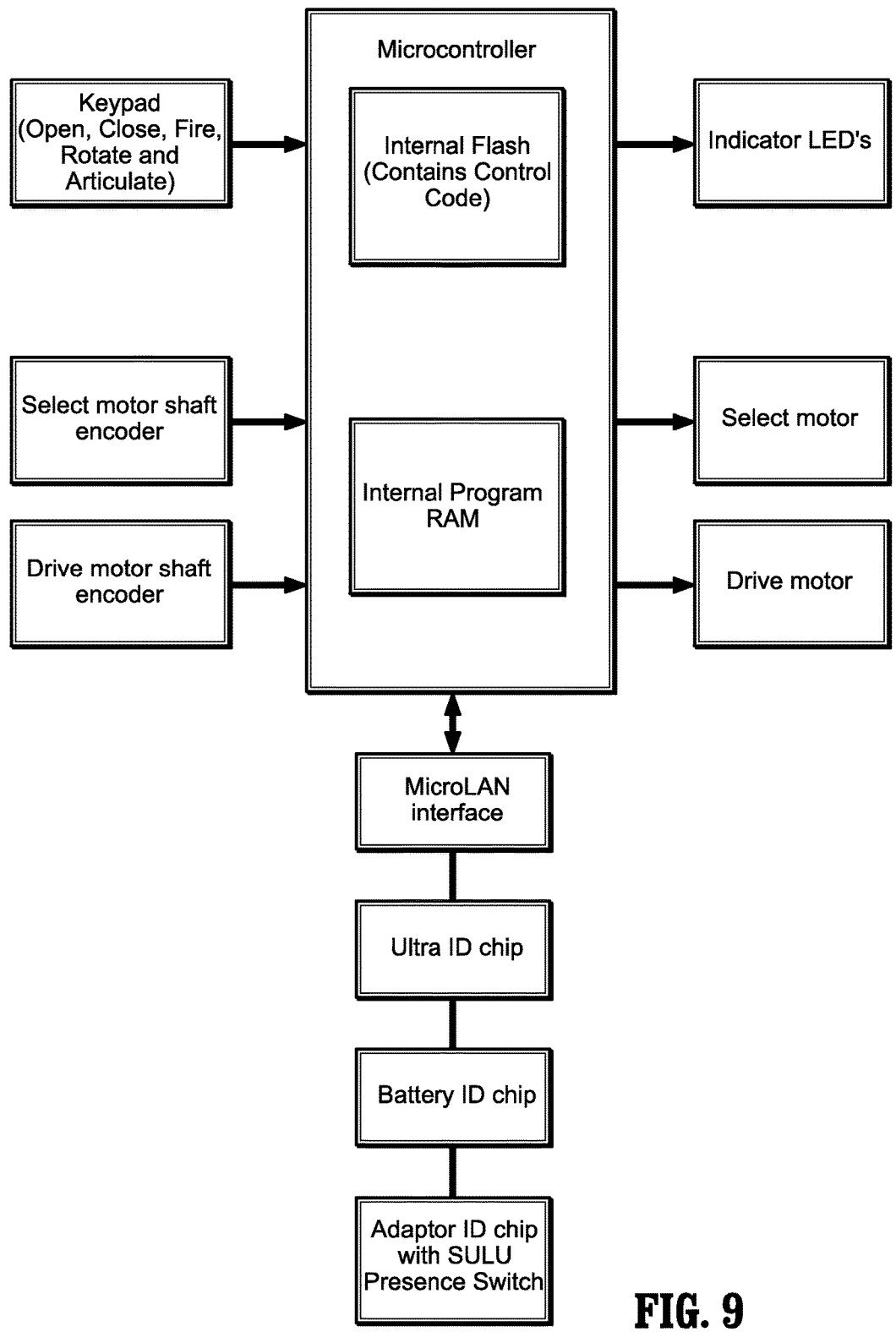
FIG. 9 is a schematic illustration of the outputs to the LED's; selection of motor (to select clamping/cutting, rotation or articulation); and selection of the drive motors to perform a function selected.

A high level electrical architectural view of the system is displayed in FIG. 9 and shows the connections to the various hardware and software interfaces. Inputs from presses of buttons 124, 126 and from motor encoders of the drive shaft are shown on the left side of FIG. 9. The microcontroller contains the device software that operates surgical device 100, adapter assembly 200 and/or end effector 300. The microcontroller receives inputs from and sends outputs to a MicroLAN, an Ultra ID chip, a Battery ID chip, and Adaptor ID chips.

The MicroLAN, the Ultra ID chip, the Battery ID chip, and the Adaptor ID chips control surgical device 100, adapter assembly 200 and/or end effector 300 as follows:
MicroLAN—Serial 1-wire bus communication to read/write system component ID information.
Ultra ID chip—identifies surgical device 100 and records usage information.
Battery ID chip—identifies the Battery 156 and records usage information.
Adaptor ID chip—identifies the type of adapter assembly 200, records the presence of an end effector 300, and records usage information.

The right side of the schematic illustrated in FIG. 9 indicates outputs to the LED's; selection of motor (to select clamping/cutting, rotation or articulation); and selection of the drive motors to perform the function selected.

As illustrated in FIGS. 1 and 8, the end effector is designated as 300. End effector 300 is configured and dimensioned for endoscopic insertion through a cannula, trocar or the like. In particular, in the embodiment illustrated in FIGS. 1 and 8, end effector 300 may pass through a cannula or trocar when end effector 300 is in a closed condition.

End effector 300 includes a proximal body portion 302 and a tool assembly 304. Proximal body portion 302 is releasably attached to a distal coupling 230 of adapter assembly 200 and tool assembly 304 is pivotally attached to a distal end of proximal body portion 302. Tool assembly 304 includes an anvil assembly 306 and a cartridge assembly 308. Cartridge assembly 308 is pivotal in relation to anvil assembly 306 and is movable between an open or unclamped position and a closed or clamped position for insertion through a cannula of a trocar.

Proximal body portion 302 includes at least a drive assembly 360 and an articulation link 366.

Referring to FIG. 8, drive assembly 360 includes a flexible drive beam 364 having a distal end which is secured to a dynamic clamping member 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of beam 364. Drive member 374 defines a proximal porthole 376 which receives connection member 247 of drive tube 246 of first drive converter assembly 240 of adapter assembly 200 when end effector 300 is attached to distal coupling 230 of adapter assembly 200.

When drive assembly 360 is advanced distally within tool assembly 304, an upper beam of clamping member 365 moves within a channel defined between anvil plate 312 and anvil cover 310 and a lower beam moves over the exterior surface of carrier 316 to close tool assembly 304 and fire staples therefrom.

Proximal body portion 302 of end effector 300 includes an articulation link 366 having a hooked proximal end 366a which extends from a proximal end of end effector 300. Hooked proximal end 366a of articulation link 366 engages coupling hook 258c of drive bar 258 of adapter assembly 200 when end effector 300 is secured to distal housing 232 of adapter assembly 200. When drive bar 258 of adapter assembly 200 is advanced or retracted as described above, articulation link 366 of end effector 300 is advanced or retracted within end effector 300 to pivot tool assembly 304 in relation to a distal end of proximal body portion 302.

As illustrated in FIG. 8, cartridge assembly 308 of tool assembly 304 includes a staple cartridge 305 supportable in carrier 316. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of surgical device 100, drive assembly 360 abuts an actuation sled and pushes actuation sled through cartridge 305. As the actuation sled moves through cartridge 305, cam wedges of the actuation sled sequentially engage staple pushers 309 to move staple pushers 309 vertically within staple retention slots 305b and sequentially eject a single staple 307 therefrom for formation against anvil plate 312.

Reference may be made to U.S. Patent Publication No. 2009/0314821, filed on Aug. 31, 2009, entitled "TOOL ASSEMBLY FOR A SURGICAL STAPLING DEVICE," the entire content of which is incorporated herein by reference, for a detailed discussion of the construction and operation of end effector 300.

Reference may also be made to U.S. patent application Ser. No. 13/484,975, filed on May 31, 2012, entitled "HAND HELD SURGICAL HANDLE ASSEMBLY, SURGICAL ADAPTERS FOR USE BETWEEN SURGICAL HANDLE ASSEMBLY AND SURGICAL END EFFECTORS, AND METHODS OF USE", the entire content of which is incorporated herein by reference, for a detailed discussion of the construction and operation of any of the remaining components of surgical device 100, adapter assembly 200, and end effector 300.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An adapter assembly for selectively interconnecting an end effector that is configured to perform a function and a surgical device that is configured to actuate the end effector, the end effector including at least one axially translatable drive member, and the surgical device including at least one rotatable drive shaft, the adapter assembly comprising:
   a housing configured and adapted for connection with the surgical device and to be in operative communication with each of the at least one rotatable drive shaft of the surgical device;
   an outer tube having a proximal end supported by the housing and a distal end configured and adapted for connection with the end effector, wherein the distal end of the outer tube is in operative communication with each of the at least one axially translatable drive member of the end effector; and
   at least one drive converter assembly for interconnecting a respective one of the at least one rotatable drive shaft of the surgical device and one of the at least one axially translatable drive member of the end effector, wherein the at least one drive converter assembly includes a first end that is connectable to a first rotatable drive shaft of the surgical device and a second end that is connectable to a first axially translatable drive member of the end effector, wherein the at least one drive converter assembly converts and transmits a rotation of the first rotatable drive shaft of the surgical device to an axial translation of the first axially translatable drive member of the end effector, wherein the at least one drive converter assembly includes:

a drive shaft rotatably disposed within the housing and the outer tube, wherein a proximal end of the drive shaft of the at least one drive converter assembly is configured to be in operative communication with the first rotatable drive shaft of the surgical device, wherein the drive shaft of the at least one drive converter assembly has a threaded distal end portion defining a plurality of turns disposed longitudinally along the drive shaft of the at least one drive converter assembly;

a drive coupling nut threadably engaged to between 25 and 35 of the plurality of turns of the threaded distal end portion of the drive shaft of the at least one drive converter assembly, the drive coupling nut being manufactured from unreinforced polyetheretherketone thermoplastic polymer, wherein the drive coupling nut is inhibited from axial rotation relative to the drive shaft of the at least one drive converter assembly; and an axially translatable drive bar having a proximal portion connected to the drive coupling nut and a distal portion configured and adapted for selective connection to the first axially translatable drive member of the end effector, wherein rotation of the first rotatable drive shaft of the surgical device results in rotation of the drive shaft of the at least one drive converter assembly, and wherein rotation of the drive shaft of the at least one drive converter assembly results in axial translation of the drive coupling nut and the axially translatable drive bar that is connected thereto.

2. The adapter assembly according to claim 1, wherein the drive coupling nut of the at least one drive converter assembly engages 29 turns of the threaded distal end portion of the drive shaft.

3. The adapter assembly according to claim 1, wherein the threaded distal end portion of the drive shaft of the at least one drive converter assembly is configured as a Unified-series thread profile.

4. The adapter assembly according to claim 1, wherein the threaded distal end portion of the drive shaft of the at least one drive converter assembly is processed by at least one of surface hardening, rolling, whirling and electro-polishing.

5. The adapter assembly according to claim 1, wherein the at least one drive converter assembly includes a first washer disposed adjacent a proximal surface of the drive coupling nut, and a second washer disposed against a distal surface of the drive coupling nut.

6. The adapter assembly according to claim 1, wherein the drive coupling nut of the at least one drive converter assembly includes at least one outer annular rib.

7. An adapter assembly for selectively interconnecting an end effector that is configured to perform a function and a surgical device that is configured to actuate the end effector, the end effector including at least one axially translatable drive member, and the surgical device including at least one rotatable drive shaft, the adapter assembly comprising:

at least one drive converter assembly for interconnecting a respective one of the at least one rotatable drive shaft of the surgical device and one of the at least one axially translatable drive member of the end effector, wherein the at least one drive converter assembly includes a first end that is connectable to a first rotatable drive shaft of the surgical device and a second end that is connectable to a first axially translatable drive member of the end effector, wherein the at least one drive converter assembly converts and transmits a rotation of the first rotatable drive shaft of the surgical device to an axial translation of the first axially translatable drive member of the end effector, wherein the at least one drive converter assembly includes:

a drive shaft rotatably disposed within the housing and the outer tube, wherein a proximal end of the drive shaft of the at least one drive converter assembly is configured to be in operative communication with the first rotatable drive shaft of the surgical device, wherein the drive shaft of the at least one drive converter assembly has a threaded distal end portion defining a plurality of turns disposed longitudinally along the drive shaft of the at least one drive converter assembly;

a drive coupling nut threadably engaged to between 25 and 35 of the turns of the threaded distal end portion of the drive shaft of the at least one drive converter assembly, the drive coupling nut being manufactured from unreinforced polyetheretherketone thermoplastic polymer, wherein the drive coupling nut is inhibited from axial rotation relative to the drive shaft of the at least one drive converter assembly; and an axially translatable drive bar having a proximal portion connected to the drive coupling nut and a distal portion configured and adapted for selective connection to the first axially translatable drive member of the end effector, wherein rotation of the first rotatable drive shaft of the surgical device results in rotation of the drive shaft of the at least one drive converter assembly, and wherein rotation of the drive shaft of the at least one drive converter assembly results in axial translation of the drive coupling nut and the axially translatable drive bar that is connected thereto.

8. The adapter assembly according to claim 7, wherein the drive coupling nut of the at least one drive converter assembly engages 29 turns of the threaded distal end portion of the drive shaft.

9. The adapter assembly according to claim 7, wherein the threaded distal end portion of the drive shaft of the at least one drive converter assembly is configured as a Unified-series thread profile.

10. The adapter assembly according to claim 7, wherein the at least one drive converter assembly includes a first washer disposed adjacent a proximal surface of the drive coupling nut, and a second washer disposed against a distal surface of the drive coupling nut.

11. The adapter assembly according to claim 7, wherein the drive coupling nut of the at least one drive converter assembly includes at least one outer annular rib.

* * * * *